United States Patent [19]

Funakoshi

[11] 4,113,712

[45] Sep. 12, 1978

[54] HBsAG PARTICLE COMPOSED OF SINGLE POLYPEPTIDE SUBUNITS AND THE PREPARATION PROCEDURE

[75] Inventor: Satoshi Funakoshi, Katano, Japan

[73] Assignee: The Green Cross Corporation, Osaka, Japan

[21] Appl. No.: 664,983

[22] Filed: Mar. 8, 1976

[51] Int. Cl.² .................. A61K 39/12; A61K 39/42; C07G 7/00; G01N 33/16

[52] U.S. Cl. .................. 260/112 R; 424/8; 424/12; 424/86; 424/89; 424/177

[58] Field of Search .................. 424/3, 8, 12, 86, 89, 424/177; 260/112 R, 112 B, 112.5

[56] References Cited

FOREIGN PATENT DOCUMENTS 75-160,420 12/1975 Japan.

OTHER PUBLICATIONS

Manual for the Handling of App'l. for Pats., Designs & T.M. Throughout the World, Octrooibureau Los en Stigter, Amsterdam, vol. 2, Supp'l. No. 27, Jul. 1972, pp. 1-3 & 7.
Gerin, J. of Virol., vol. 4, 1969, pp. 763-768.
Barker, J. of Virol, vol. 14, 1974, pp. 1552-1558.
Dreesman, The Amer. J. of the Med. Sci., vol. 270, No. 1, Jul.-Aug., 1975, pp. 123-129.

Primary Examiner—Albert T. Meyers
Assistant Examiner—A. P. Fagelson
Attorney, Agent, or Firm—Cushman, Darby & Cushman

[57] ABSTRACT

Hepatitis B surface antigen particles composed of single polypeptide subunits having a molecular weight of about 55,000 dalton are prepared by heating hepatitis B surface antigen in isotonic sodium chloride solution at about neutral pH containing a surfactant capable of delipidation such as alkali-metal salts of bile acids or of lauroylsarcosinic acid, or poloxyethylene alkylphenol containing an average oxyethylene of 7 to 10 molecules, or polyoxyethylene sorbitan monoalkylester containing an average oxyethylene of 20 molecules.

A uniform hepatitis B surface antigen particle thus obtained has a spherical form 18 to 22 nm in diameter with an empty core, a molecular weight of about 2,200,000 dalton, and the characteristic of low toxicity.

This hepatitis B surface antigen particle is useful for the preparation of vaccines, as a standard antigen reagent for testing hepatitis B surface antigen and the antibody, and as an antigen for immunizing animals to obtain a highly specific and strong antibody.

8 Claims, 1 Drawing Figure

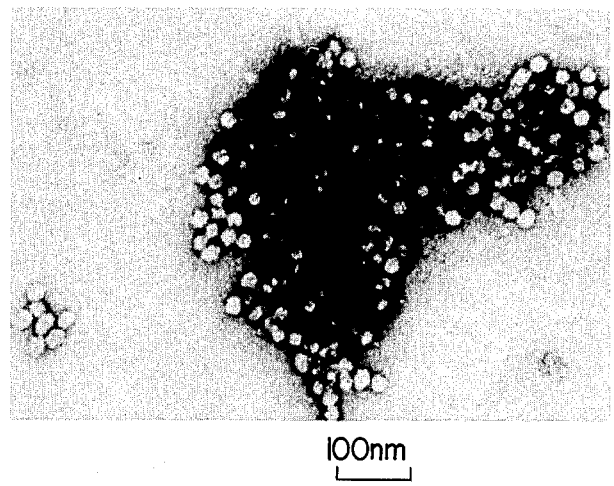
100nm

HBsAG PARTICLE COMPOSED OF SINGLE POLYPEPTIDE SUBUNITS AND THE PREPARATION PROCEDURE

This invention relates to a uniform hepatitis B surface antigen spherical particle which retains the original antigenicity of hepatitis B surface antigen, and to its method of preparation from highly purified hepatitis B surface antigen obtained from human plasma or other materials containing hepatitis B surface antigen.

According to the regulations of the World Health Organization, the hepatitis B antigen was designated as HBAg, but now it has been found that the hepatitis B antigen is divided into two portions, one of which is infective and designated as hepatitis B core antigen, and the other of which is the outer shell of the virus lacking infectiveness and is designated as hepatitis B surface antigen, which was detected as hepatitis B antigen before this present invention.

The uniform hepatitis B surface antigen spherical particle referred to in this invention is a protein retaining the original antigenicity of hepatitis B surface antigen and is a spherical particle of 18 to 22 nm diameter, of which the inside is empty or is of low density core, according to electron microscopic observation. The molecular weight of the uniform hepatitis B surface antigen spherical particle is supposedly about 2,200,000 dalton composed of single polypeptide subunits of molecular weight of about 55,000 dalton. The uniform hepatitis B surface antigen spherical particle of the present invention is referred to as HBsAg$_{55}$ (hepatitis B surface antigen$_{55}$) hereinafter.

Hepatitis B surface antigen, formerly hepatitis B antigen, is known to be related to HBV hepatitis B virus and responsible for serum hepatitis or B type hepatitis infection. Plasma or serum containing HBsAg often causes troublesome hepatitis in patients infused with the solution and in physicians, technicians or any employees who have a chance to contact such solution.

Hitherto hepatitis B surface antigen has been obtained in relatively pure form from human plasma or its derivatives by collecting the fraction having a density ranging from 1.20 to 1.23 g/cm$^3$ formed by the density gradient ultracentrifugal method (J. L. Gerin, P. V. Holland and R. H. Purcell; Journal of Virology, 7, 569 – 576, 1971, and N. Sukeno, R. Shirachi, J. Yamaguchi and N. Ishida; Journal of Virology, 9, 182 – 183, 1972).

Recently, affinity chromatographic technique has been proposed to be a good method for the purification of hepatitis B surface antigen. The outline of this method is as follows.

The species of animal used for the process are optional. For example, goat anti-hepatitis B surface antigen serum is obtained by immunizing a goat with purified hepatitis B surface antigen. This antiserum is added to human serum free of hepatitis B surface antigen so as to absorb and precipitate antibodies to human serum components. The supernatant is then subjected to ammonium sulfate fractionation to obtain anti-hepatitis B surface gamma globulin.

The anti-hepatitis B surface gamma globulin is then coupled to Sepharose 4B (produced by Pharmacia Co., Sweden) activated with cyanogen bromide to prepare immobilized anti-hepatitis B surface. The immobilized anti-HBs so prepared is packed in a column.

Human serum or plasma containing hepatitis B surface antigen or a clear solution separated from a suspension in 0.01 M phosphate buffer of an alpha- and beta-globulin fraction prepared from the plasma containing hepatitis B surface antigen by a conventional method, such as by ethanol, ammonium sulfate or acrinol fractionation is subjected to the above-said column by usual affinity chromatographic technique.

Hepatitis B surface antigen stuck in the column is eluted with 0.4 M glycine-HCl buffer solution of pH 2.5. The eluate is dialysed against 0.01 M phosphate buffer.

The resulting solution containing hepatitis B surface antigen is then subjected to chromatography using a column prepared with immobilized horse anti-human plasma gamma globulin by the same technique as above.

This step effects the removal of trace amounts of contaminants by holding them in the column and the collection of hepatitis B surface antigen in the eluting solution.

Hepatitis B surface antigen thus obtained has an electrophoretic property similar to that of alpha or beta globulin, and is observed electron microscopically as a mixture of three different forms of particles: small spherical particles about 20 nm in diameter, tubular particles about 20 nm in diameter and large spherical particle about 42 nm in diameter with a core.

It is reported by many investigators on testing peptides generated by cleaving the hepatitis B surface antigen particle by various methods that hepatitis B surface antigen is composed of multiple subunits of different molecular weight polypeptides.

That is, Gerin, et. al (loc., cit.) have reported that hepatitis B surface antigen is composed of three different polypeptides of molecular weights of 26,000, 32,000 and 40,000 dalton. Also there has been reported, 25,000 and 32,000 dalton polypeptides by Vyas et. al. (G. N. Vyas, E. W. Williams, G. G. B. Klaus and H. E. Bond, the Journal of Immunology, 108, 1114 – 1118, 1972), 39,000, 32,000, 27,000, 22,000 and trace amounts of 16,000 and 10,000 dalton polypeptides by Dressmann et. al. (G. R. Dressmann, F. B. Hollinger, J. R. Suriano, R. S. Fujioka, J. P. Brunschwig and J. L. Melnik, Journal of Virology, 10, 469 – 476, 1972), 100,000, 65,000, 36,000 and 20,000 dalton polypeptides by Howard and Zuckerman (C. R. Howard and A. J. Zuckerman, Hepatitis Memoranda, H-576, October, 1973, U.S.A.) and 25,000, 28,000 and 33,000 dalton polypeptides by Sukeno et. al. (N. Sukeno, S. Aikawa and N. Ishida, Hepatitis Memoranda, H-292, April, 1972, U.S.A.). To demonstrate these subunits, Sukeno et. al. employed a technique to cleave the hepatitis B surface antigen molecule by sodium dodecylsulfate (SDS) in urea solution, which technique is referred to as "measurement of molecular weights by electrophoresis on SDS-acrylamide gel" (Colowik-Kaplan, Methods in Enzymology, vol. 26, pp. 3, 1972).

This invention made it possible to convert such complicated hepatitis B surface antigen molecule to a uniform spherical particle of 18 to 22 nm diameter (HBsAg$_{55}$) composed of single polypeptide subunits of molecular weight 55,000 dalton, which retained its original antigenicity, by treating hepatitis B surface antigen with certain surfactants capable of delipidation.

The object of this invention is to offer a solution containing hepatitis B surface antigen particles composed of single polypeptide subunits, having a molecular weight of about 55,000 dalton or the equivalent, and a spherical form of 18 to 22 nm diameter with an empty core of molecular weight of about 2,200,000 (HBsAg$_{55}$) and the method of its preparation.

The other objects and benefit of this invention will be clarified by the following explanation.

There is proposed by this invention the method of preparing and isolating HBsAg$_{55}$ by heating hepatitis B surface antigen in isotonic sodium chloride solution containing a surfactant capable of delipidation and to obtain the solution of HBsAg$_{55}$.

Hepatitis B surface antigen material used in this invention can be obtained from serum or plasma in relatively pure form by the aforesaid known methods, however, it is the most beneficial to use a fraction of alpha- and beta-globulins as a starting material, for example, fraction IV-1 processed by Cohn's ethanol fractionation method. The thus obtained hepatitis B surface antigen is used as it is or, preferably, after further purification.

That is, hepatitis B surface antigen obtained by the said known procedures is recommended to be further freed from contaminants of small molecules by subjecting it to gel filtration using hydrophilic gels suitable for separating substances of molecular weight of from 3,000 to 150,000 such as dextran gel (for example, Sephadex G-200 supplied by Pharmacia Co., Sweden), polyacrylamide gel (for example, Biogel P-300 supplied by Bio-Rad Co.) or agarose gel (for example, Sepharose 6B supplied by Pharmacia Co., Sweden). Gel filtration is carried out at pH 6 to 8 in isotonic sodium chloride solution.

Surfactants capable of delipidation used in this invention are chosen from anionic surfactants of the carboxylic acid type such as alkali-metal salts of bile acids like sodium deoxycholate, glycocholate, taurocholate and dehydrocholate and of lauroylsarcosinic acid, such as sodium lauroylsarcosinate, surfactants of the polyoxyethylene alkylphenol type containing an average of 7 to 10 molecules of oxyethylene, such as polyoxyethylene octylphenol, and surfactants of the polyoxyethylene sorbitan monoalkyl ester type containing an average of 20 molecules of oxyethylene, such as polyoxyethylene sorbitan monooleate.

Hepatitis B surface antigen in isotonic sodium chloride solution of pH range from 5 to 9 (preferably 7.2) containing 0.05 to 5% (preferably 0.5% for most cases) of a surfactant is heated for 5 to 120 minutes (preferably 30 minutes) at 40° to 80° C (preferably 60° C). Practically isotonic buffered saline of a fixed pH containing hepatitis B surface antigen is added with a specified amount of surfactant. The pH of the mixed solution is adjusted, if necessary. The solution is then heated for a fixed period at a fixed temperature. This treatment causes the modification of the molecule of hepatitis B surface antigen to a uniform HBsAg$_{55}$ molecule.

The generated HBsAg$_{55}$ is then isolated from other proteins by methods known for the separation of a protein of a certain molecular weight from a mixture such as ion exchange chromatography, fractional precipitation, etc. However, the gel filtration method is recommended because this method is simple and gives good results. Any gel suitable for the separation of proteins having molecular weights of between 3,000 and 150,000 dalton is used for this purpose. The gel equilibrated with the same solution as HBsAg$_{55}$ is packed in a column. The HBsAg$_{55}$ solution is passed through this column. HBsAg$_{55}$ is collected in the effluent of the void volume.

The fraction containing HBsAg$_{55}$ so collected is concentrated, if necessary. Highly purified HBsAg$_{55}$ solution is then obtained after removing the surfactant used by dialysing against isotonic buffered saline or by the technique of gel filtration on a suitable gel for the separation of substances of low molecular weight such as Sephadex G50.

HBsAg$_{55}$ has sufficient strength of the original antigenicity. HBsAg$_{55}$ is a uniform spherical particle of 18 to 22 nm diameter of which the inside looks empty or has a low density core by electron microscopic observation.

HBsAg$_{55}$ is further analysed electrophoretically by the method of "measurement of molecular weights by electrophoresis on SDS-acrylamide gel" (loc. cit.).

One volume of 0.01 M phosphate buffer solution (pH 7.0) of HBsAg$_{55}$ and nine volumes of 0.01 M phosphate buffer solution (pH 7.0) each containing 1% of SDS and 2-mercapto-ethanol are mixed and heated for 2 minutes at 100° C. The concentration of HBsAg$_{55}$ is determined by optical density at 280 nm ($E_{280\ nm}$) to be between 1 and 10. This heat treated solution is subjected to the SDS-polyacrylamide gel electrophoresis in which 7.5% polyacrylamide gel made up in 0.1 M phosphate buffer solution of pH 7.6 containing 0.1% SDS and 4 M urea is used. Serum albumin (mol. wt. 68,000), catalase (mol. wt. 58,000), ovalbumin (mol. wt. 43,000) and egg white lysozyme (mol. wt. 14,300) are used as the markers. HBsAg$_{55}$ reveals a single component of molecular weight of about 55,000 dalton by this analysis.

This suggests that HBsAg$_{55}$ is composed of 40 single subunits of molecular weight of about 55,000 dalton on the basis that the molecular weight proposed for 20 nm spherical particles of HBsAg is about 2,200,000 dalton.

The attached photo illustrates the electron microscopic observation of HBsAg$_{55}$ particles obtained by this invention. Each particle (designated as 1) is HBsAg$_{55}$ and the dark area in the middle of the particle is empty core.

Since HBsAg$_{55}$ referred to in this invention is obtained as a modified and highly purified form of hepatitis B surface antigen and retains the original antigenicity of hepatitis B surface antigen, even if the preparation is still responsible for infection, or is still contaminated by a very trace amount of infectious hepatitis B virus, the HBsAg$_{55}$ preparation can be used as an excellent and low toxic vaccine if a simple and known inactivating heat-treatment for hepatitis B virus is employed.

The HBsAg$_{55}$ is also a superb source material for preparing hapten by cleaving the molecule enzymatically (J. M. Steward, J. D. Young and I. E. Benjamin. Biochemistry, 5, 3396, 1966) or chemically, since the HBsAg$_{55}$ molecule is composed of single subunits.

HBsAg$_{55}$ is, of course, useful as a standard reagent for testing HBsAg and the antibody (anti-hepatitis B surface) and as an antigen for immunizing animals to produce antisera against hepatitis because of its purity and single subunit composition.

The present invention is illustrated in detail below with reference to the examples, but the examples do not limit the ranges of this invention.

EXAMPLE 1

A purified hepatitis B surface antigen preparation was obtained from 1 liter of pooled hepatitis B surface antigen positive plasma by the ultracentrifugal method. The titer of hepatitis B surface antigen of this preparation was 1 : 4096/0.1 mg N by the complement fixation (CF) test method. This preparation revealed three different polypeptide subunits of molecular weighs 25,000, 28,000 and 33,000 dalton by SDS-polyacrylamide gel electrophoretic analysis.

Five milliliters of the purified hepatitis B surface antigen solution in 0.01 M tris-HCl buffer of pH 7.5 containing 0.15 M sodium chloride were subjected to gel filtration on a 2.5 × 45 cm column of Sephadex G200. The first fraction of 17 ml which contained hepatitis B surface antigen was collected. After the solution was concentrated down to 6 ml, sodium deoxycholate (NaDOC) was added to the solution to a final concentration of 0.5% and the solution heated for 30 minutes at 60° C. The heat treated solution was then equilibrated with 0.01 M Tris-HCl buffer solution of pH 8.0 containing 0.15 M sodium chloride and 0.01 M NaDOC and subjected to gel filtration on a 2.5 × 45 cm column of Sephadex G200. The first fraction of 20 ml which contained hepatitis B surface antigen ($HBsAg_{55}$) was collected and further fractionated on a 1.5 × 60 cm column of Sephadex G50 to remove NaDOC. The solution was concentrated to 2 ml by the vacuum dialysis technique. $HBsAg_{55}$ present in this solution was demonstrated microscopically as spherical particles of 18 to 22 nm diameter with an empty core and single polypeptide of molecular weight 55,000 dalton was revealed by SDS-polyacrylamide gel electrophoretic analysis. The CF titer as hepatitis B surface antigen was 1 : 8192/0.1 mg N and the recovery on the basis of $E_{280\,nm}$ was 6.4%.

EXAMPLE 2

A purified hepatitis B surface antigen preparation was obtained from 10 liters of pooled hepatitis B surface antigen positive plasma by the affinity chromatographic method. The CF titer of the antigen was 1 : 2048/0.1 mg N. This preparation revealed seven different polypeptide subunits of molecular weights 17,000, 25,000, 28,000, 33,000, 40,000, 52,000 and 60,000 dalton by SDS-polyacrylamide gel electrophoretic analysis.

Thirty milliliters of the purified hepatitis B surface antigen solution in 0.05 M phosphate buffered saline (pH 7.2) were subjected to gel filtration on a 5 × 90 cm column of Biogel P-300. The first fraction of 150 ml which contained hepatitis B surface antigen was collected. After the solution was concentrated down to 16 ml, polyoxyethylene (9) octylphenol was added to the solution to the final concentration of 1% and the solution heated for 20 minutes at 70° C.

The heat treated solution was equilibrated with 0.05 M phosphate buffered saline of pH 7.2 containing 0.02 M polyoxyethylene (9) octylphenol and subjected to gel filtration on a 3.5 × 90 cm column of Sepharose 6B. The first fraction of 42 ml which contained hepatitis B surface antigen ($HBsAg_{55}$) was collected and vacuum dialysed against isotonic saline to obtain 10 ml of $HBsAg_{55}$ solution. $HBsAg_{55}$ of this solution was observed electron microscopically as spherical particle of 18 to 22 nm diameter with an empty core, and single polypeptide of molecular weight 55,000 dalton was revealed by SDS-polyacrylamide gel electrophoretic analysis. The CF titer of hepatitis B surface antigen was 1 : 4096/0.1 mg N and the recovery on the basis of $E_{280}$ nm was 5.8%.

EXAMPLE 3

Example 1 was repeated except that 0.5% sodium lauroylsarcosinate was used instead of 0.5% sodium deoxycholate and the heat treatment was effected for 100 minutes at 45° C instead of 30 minutes at 60° C. The purified $HBsAg_{55}$ obtained by this method had the same properties as shown in Example 1. The recovery was 4.2% and the CF titer of hepatitis B surface antigen was 1 : 4096/0.1 mg N.

EXAMPLE 4

Example 1 was repeated except that 1.2% polyoxyethylene (20) sorbitan monooleate was used instead of 0.5% sodium deoxycholate and heat treatment was effected for 60 minutes at 60° C instead of 30 minutes at 60° C. The purified $HBsAg_{55}$ obtained by this method had the same properties as shown in Example 1. The recovery was 4.0% and the CF titer of hepatitis B surface antigen was 1 : 4096/0.1 mg N.

What is claimed is:

1. A method for the preparation of uniform size hepatitis B surface antigen particles composed of single polypeptide subunits of molecular weight of 55,000 dalton ($HBsAg_{55}$) comprising heating hepatitis B surface antigen for 5 to 120 minutes at 40° to 80° C with a surfactant selected from the group consisting of alkali metal salts of bile acids, alkali metal salts of lauroyl sarcosinic acid, polyoxyethylene alkyl phenol containing an average of 7 to 10 molecules of oxyethylene and polyoxyethylene sorbitan monoalkylester containing an average of 20 molecules of oxyethylene capable of delipidation in isotonic sodium chloride solution at about neutral pH, collecting by gel filtration using a gel of dextran, polyacrylamide or agarose, said antigen particles having a molecular weight of about 2,200,000 dalton as an aqueous solution, and removing surfactant from said aqueous antigen particles solution by dialysis or gel filtration.

2. The method of claim 1 wherein the surfactant is sodium deoxycholate, sodium glycocholate, sodium taurocholate or sodium dehydrocholate.

3. The method of claim 1 wherein the surfactant is sodium lauroyl sarcosinate.

4. The method of claim 1 wherein the surfactant is polyoxyethylene (9) octylphenol.

5. The method of claim 1 wherein the surfactant is polyoxyethylene (2) sorbitan monooleate.

6. The method of claim 1 wherein the concentration of surfactant in isotonic solution is 0.05 to 5%.

7. The method of claim 6 wherein the concentration of surfactant in isotonic solution is about 0.5%.

8. A uniform hepatitis B surface antigen spherical particle of 18 to 22 nm diameter with an empty core having a molecular weight of about 2,200,000 dalton composed of single polypeptide subunits having a molecular weight of about 55,000 dalton prepared by the process of claim 1.

* * * * *